(12) United States Patent
Kamada

(10) Patent No.: US 8,496,330 B2
(45) Date of Patent: Jul. 30, 2013

(54) OPHTHALMOLOGIC IMAGING APPARATUS AND METHOD FOR CONTROLLING THE SAME

(75) Inventor: Shohhei Kamada, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 158 days.

(21) Appl. No.: 13/047,633

(22) Filed: Mar. 14, 2011

(65) Prior Publication Data

US 2011/0228220 A1 Sep. 22, 2011

(30) Foreign Application Priority Data

Mar. 16, 2010 (JP) ................................. 2010-059430

(51) Int. Cl.
- *A61B 3/14* (2006.01)
- *A61B 3/10* (2006.01)
- *A61B 3/00* (2006.01)

(52) U.S. Cl.
USPC ............................ 351/206; 351/221; 351/246

(58) Field of Classification Search
USPC .................................. 351/205, 206, 221, 246
See application file for complete search history.

(56) References Cited

U.S. PATENT DOCUMENTS

| | | | |
|---|---|---|---|
| 4,690,525 | A | 9/1987 | Kobayashi |
| 5,530,494 | A | 6/1996 | Ogawa |
| 6,244,710 | B1 | 6/2001 | Ogawa |

FOREIGN PATENT DOCUMENTS

| | | |
|---|---|---|
| CN | 1977762 A | 6/2007 |
| JP | 60-137347 A | 7/1985 |
| JP | 61-203937 A | 9/1986 |
| JP | 02-237536 A | 9/1990 |
| JP | 03-114434 A | 5/1991 |
| JP | 04-150831 A | 5/1992 |
| JP | 05-192299 A | 8/1993 |
| JP | 08-033612 A | 2/1996 |
| JP | 11-238129 A | 8/1999 |
| JP | 2000-107133 A | 4/2000 |
| JP | 2000-197608 A | 7/2000 |
| JP | 2001-258852 A | 9/2001 |
| JP | 2003-010134 A | 1/2003 |
| JP | 2005-261447 A | 9/2005 |
| JP | 2005-261449 A | 9/2005 |
| JP | 2005-270152 A | 10/2005 |
| JP | 2005-279154 A | 10/2005 |

*Primary Examiner* — Jack Dinh

(74) *Attorney, Agent, or Firm* — Canon U.S.A., Inc., IP Division

(57) ABSTRACT

An ophthalmologic imaging apparatus includes: a control unit configured to control, based on a pixel value of the optic papilla in an infrared light image of the fundus of a subject's eye to which infrared light is radiated, the light amount of visible light to be radiated onto the subject's eye; and an imaging unit configured to capture an image of the fundus of the subject's eye to which visible light having the controlled light amount is radiated.

18 Claims, 11 Drawing Sheets

FIG.2A
EXEMPLARY TABLE INFORMATION
| RATIO OF REFLECTED LIGHT AMOUNT FROM OPTIC PAPILLA TO RADIATED INFRARED LIGHT AMOUNT | MAXIMUM IMAGING LIGHT AMOUNT THAT DOES NOT CAUSE OVER-EXPOSED OPTIC PAPILLA |
|---|---|
| . . . . | . . . . |
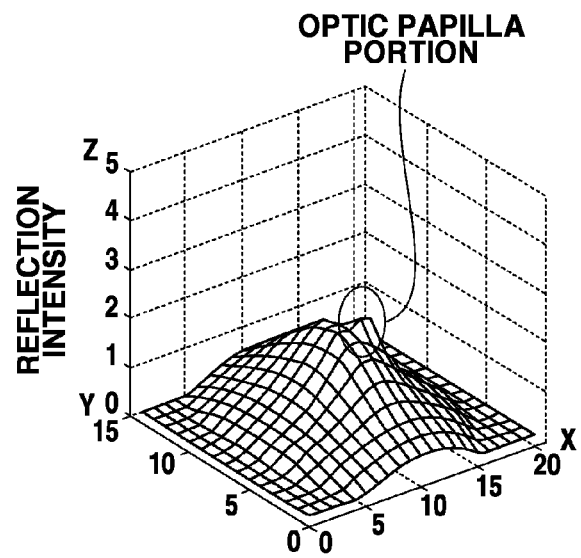
FIG.2B
INFRARED LIGHT REFLECTION INTENSITY OF FUNDUS
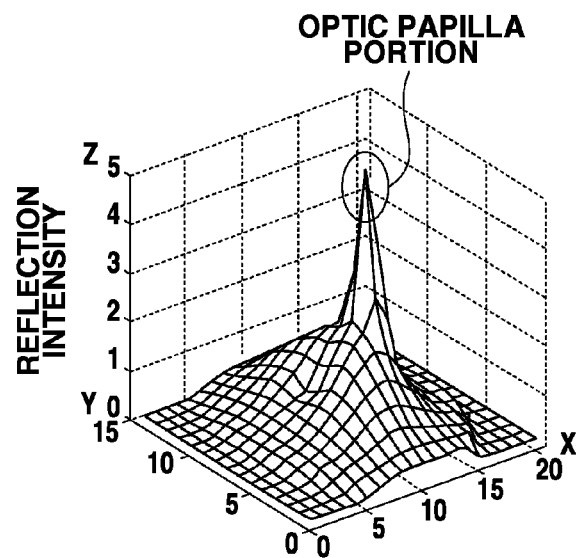
FIG.2C
VISIBLE LIGHT REFLECTION INTENSITY OF FUNDUS

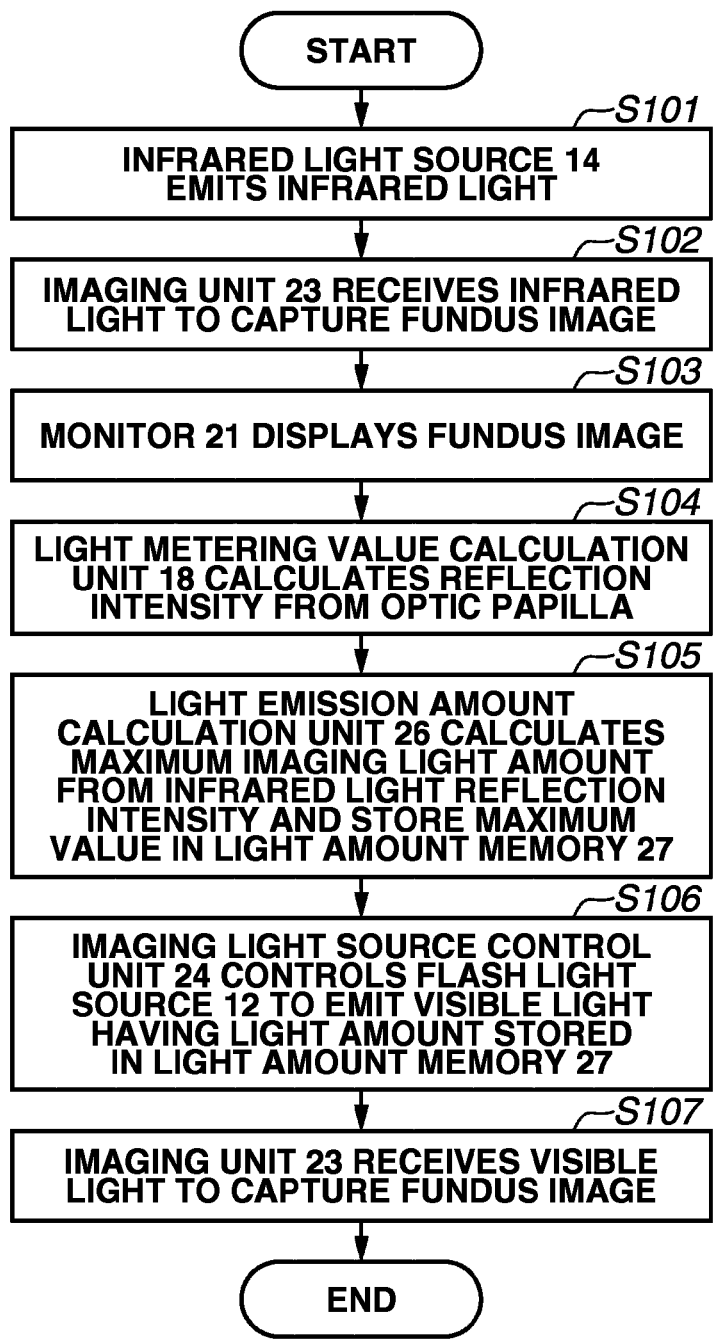

OPHTHALMOLOGIC IMAGING APPARATUS AND METHOD FOR CONTROLLING THE SAME

BACKGROUND OF THE INVENTION

1. Field of the Invention

The present invention relates to an ophthalmologic imaging apparatus such as a fundus camera which controls the light amount to be received by an image sensor.

2. Description of the Related Art

A conventional ophthalmologic imaging apparatus is known, which radiates imaging light such as visible light onto the fundus of a subject's eye and receives reflected light therefrom to capture a fundus image. Since the reflectance of the fundus differs for each subject's eye because of individual difference and pathological changes, there is provided a technique for suitably controlling the light amount of imaging light to be received by an image sensor.

As an example of such a technique, Japanese Patent Application Laid-Open No. 04-150831 discusses a technique for determining the light amount of visible light (imaging light) based on infrared light radiated onto a subject's eye and reflected by the fundus. However, this technique has a problem that the optic papilla is over-exposed in the captured fundus image since its large reflectance is not taken into consideration.

Japanese Patent Application Laid-Open No. 2005-270152 discusses a technique for setting the light amount with which the optic papilla is not over-exposed as the light amount of visible light (imaging light), based on the light amount of reflected visible light from the optic papilla of the fundus out of visible light radiated onto a subject's eye. This technique has a problem that visible light radiation before imaging causes myosis of the subject's eye.

SUMMARY OF THE INVENTION

According to an aspect of the present invention, an ophthalmologic imaging apparatus includes: a control unit configured to control, based on a pixel value of the optic papilla in an infrared light image of the fundus of a subject's eye to which infrared light is radiated, the light amount of visible light to be radiated onto the subject's eye; and an imaging unit configured to capture an image of the fundus of the subject's eye to which visible light having the controlled light amount is radiated.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 2A illustrates table information about an association between the light amount of infrared light reflected by the optic papilla and the maximum light amount of visible light to be radiated onto a subject's eye. FIG. 2B is a graph illustrating the infrared light reflection intensity of the fundus. FIG. 2C is a graph illustrating the visible light reflection intensity of the fundus.

FIG. 3 is a flow chart illustrating processing performed by the fundus camera according to the first exemplary embodiment.

FIG. 8A illustrates a case where the correct light amount Vmr of the optic papilla is greater than the minimum light amount Vgb of the fundus. FIG. 8B illustrates a case where the correct light amount Vmr of the optic papilla is smaller than the minimum light amount Vgb of the fundus. FIG. 8C illustrates a case where the maximum light amount Vmu of the optic papilla is greater than the correct light amount Vgr of the fundus. FIG. 8D illustrates a case where the maximum light amount Vmu of the optic papilla is smaller than the correct light amount Vgr of the fundus.

DESCRIPTION OF THE EMBODIMENTS

Various exemplary embodiments, features, and aspects of the invention will be described in detail below with reference to the drawings.

Figure 1:
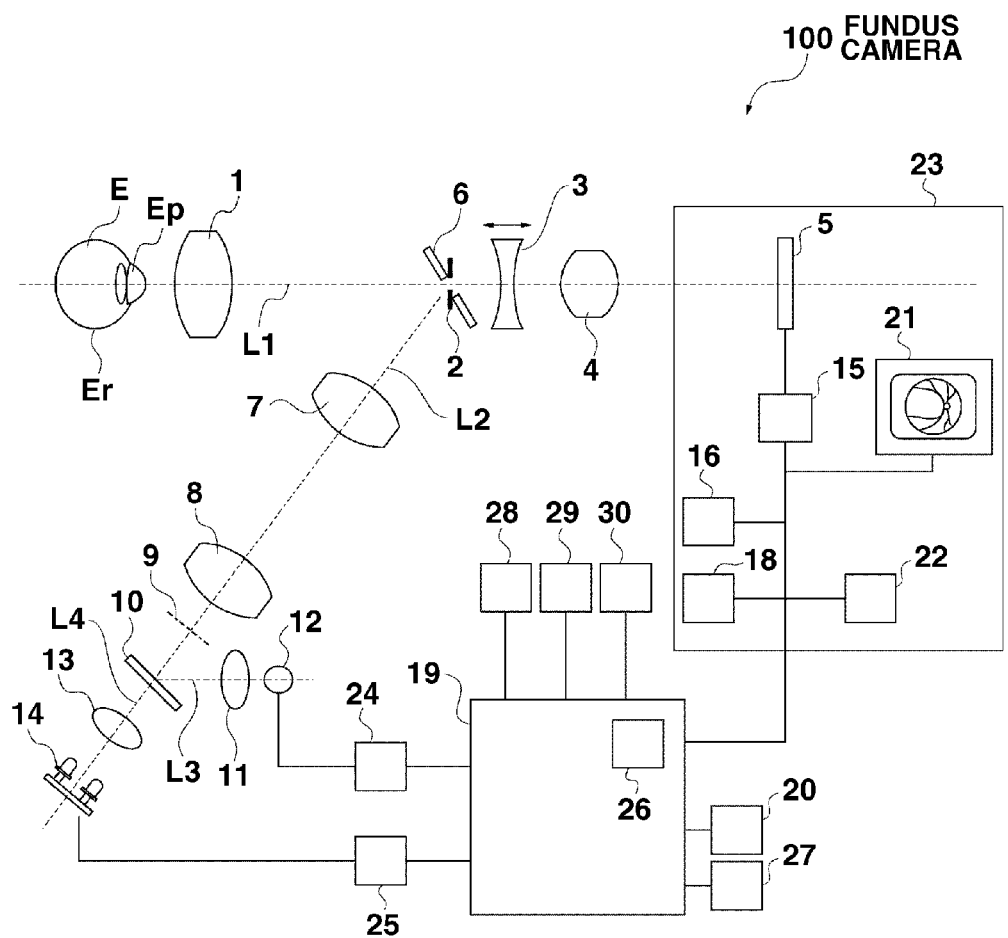
FIG. 1 illustrates a configuration of a fundus camera according to a first exemplary embodiment.

A configuration of a fundus camera 100, an exemplary ophthalmologic imaging apparatus according to a first exemplary embodiment of the present invention, will be described below with reference to FIG. 1. The fundus camera 100 includes a fundus image observation imaging unit including an observation imaging optical system and an imaging unit 23, a fundus illumination unit including a fundus illumination optical system and a light source, and a central control unit 19.

The observation imaging optical system includes an object lens 1 disposed facing a subject's eye E, an imaging diaphragm 2 disposed on an optical axis L1 of the object lens 1, and a focal lens 3, and an imaging lens 4. The observation imaging optical system is configured to guide reflected light from the fundus to an image sensor 5. When radiating infrared light, the observation imaging optical system guides reflected infrared light from the entire fundus to the image sensor 5. When radiating visible light, the observation imaging optical system guides reflected visible light from the fundus to the image sensor 5.

The imaging unit 23 receives light from the illuminated fundus to capture a fundus image. The imaging unit 23 includes the image sensor 5 having sensitivity to visible light and infrared light, an A/D conversion element 15, a memory 16, a light metering value calculation unit 18, and a imaging control unit 22. The imaging unit 23 is detachably fixed to the chassis of the optical unit of the fundus camera 100 by a mounting portion (not illustrated).

The image sensor 5 outputs an electrical signal according to the light amount of infrared light or visible light received thereby. The A/D conversion element 15 converts the electrical signal into digital form. The converted digital signal is stored in the memory 16, and at the same time output to the light metering value calculation unit 18. An infrared light image or a visible light image of the fundus is generated from the digital signal.

The light metering value calculation unit 18 acquires pixel values of an area for the optic papilla from the output electrical signal or the image data generated from the electrical signal. Based on the combination of the observation imaging optical system and the imaging unit 23, the fundus image observation imaging unit illuminates the fundus and captures a fundus image.

The fundus illumination optical system includes the object lens 1, the imaging diaphragm 2, a perforated mirror 6, lenses 7 and 8, a ring diaphragm 9, a dichroic mirror 10, and condenser lenses 11 and 13. The fundus illumination optical system guides infrared light and visible light to the subject's eye E. The perforated mirror 6 is obliquely disposed in the vicinity of the imaging diaphragm 2. The lenses 7 and 8 are disposed on an optical axis L2 extending in the reflection direction of the perforated mirror 6.

The ring diaphragm 9 having a ring-like opening has a light shielding portion at the center of the optical axis. The ring diaphragm 8 is disposed at an optically conjugate position with a pupil Ep of the subject's eye E by the lenses 7 and 8. The dichroic mirror 10 is characterized in transmitting infrared light and reflecting visible light. The dichroic mirror 10 and the ring diaphragm 9 are disposed on the optical axis L2.

A condenser lens 11 and a flash light source 12 are disposed on an optical axis L3 extending in the reflection direction of the dichroic mirror 10. A condenser lens 13 and an infrared light source 14 are disposed on an optical axis L4 extending in the transmission direction thereof.

The flash light source 12 (a visible light source) is a imaging light source for emitting visible pulse light and radiating it onto the subject's eye E. The flash light source 12 is controlled by the imaging light source control unit 24. The infrared light source 14 including a plurality of infrared ray light emitting diodes (LEDs) is an observation light source for emitting infrared steady light and radiating it onto the subject's eye E. The infrared light source 14 is controlled by an observation light source control unit 25.

An imaging light source refers to a light source which illuminates the fundus to capture a target fundus image. An observation light source refers to a light source which radiates light onto the subject's eye before capturing the target fundus image. Prior to main imaging by irradiating visible light, an examiner observes the fundus by using infrared still images and moving images obtained by radiating infrared light, and performs adjustment of position, focus, and other imaging conditions.

In the present exemplary embodiment, the flash light source 12 is a light source for 420-750 nm wide wavelength band, and the infrared light source 14 is an infrared light source for 850 nm practically single wavelength band or 50 nm narrow wavelength band. A light source having other wavelength bands may be used.

The fundus illumination optical system, the flash light source 12 (a visible light source), and the infrared light source 14 constitute the fundus illumination unit which radiates infrared light and visible light onto the subject's eye E to illuminate the fundus.

The fundus image observation imaging unit and the fundus illumination unit are retained by one chassis to constitute the optical unit of the fundus camera 100. The optical unit of the fundus camera 100 is placed on a sliding table (not illustrated) to enable position adjustment relative to the subject's eye E.

The central control unit 19 includes a central processing unit (CPU) to control the entire apparatus. The central control unit 19 also serves as a light emission amount calculation unit 26, and is connected with the light metering value calculation unit 18, an image memory 20, a light amount memory 27, a light amount control selection unit 28, an operation unit 29, and an imaging switch 30. The central control unit 19, the imaging light source control unit 24, the observation light source control unit 25, and the control selection unit 28 constitute the control unit of the fundus camera 100.

The light emission amount calculation unit 26 divides the pixel value for the optic papilla calculated by the light metering value calculation unit 18 by the light amount of infrared light radiated onto the subject's eye E by the infrared light source 14 to acquire the infrared light reflectance value of the optic papilla. Based on this value, the light emission amount calculation unit 26 determines the light amount of visible light to be radiated onto the subject's eye E. The light amount refers to the radiant energy radiated onto a unit area within a fixed period of time. It is a time-integration of a light flux $\phi v$ over a given time period $\Delta t$.

The fundus camera 100 according to the present exemplary embodiment opens the shutter (not illustrated) from a timing before radiation from the visible light source 12 until a timing after radiation, and adjusts the time period during which visible light is emitted from the visible light source 12, thus adjusting the light amount of visible light to be received by the image sensor 5. The method for adjusting the light amount of imaging light to be received by the image sensor 5 is not limited thereto. It is also possible to adjust the light intensity of the light source 12 or the time period during which the shutter is open (shutter speed).

The storage unit of the central control unit 19 stores table information which defines an association between the infrared light reflectance value of the optic papilla and the maximum light amount of imaging light to be radiated onto the fundus of the subject's eye E. This maximum value is preset as a light amount with which the optic papilla is not overexposed. With reference to the table information, the light emission amount calculation unit 26 selects the maximum imaging light amount corresponding to the measured reflectance. The table information will be described below.

Although the term "reflectance of the optic papilla" is used, reflected light from the optic papilla actually decreases because of influence of the crystalline lens and vitreous body. The luminance of the optic papilla on an image includes stray light from areas other than the optic papilla.

In the strict sense, the reflectance refers to the reflectance at the boundary face of the optic papilla free from the above-mentioned influences. However, in the present specification, the ratio of the light amount received by the image sensor 5 to the light amount emitted by the light source is used as the reflectance value. In this case, reflection also means dispersion.

The control selection unit 28 receives an instruction regarding a selection from the operation unit 29, and selects or switches a method for controlling the visible light amount. The operation unit 29 is provided to input an instruction from the examiner. For example, the operation unit 29 includes a joy stick, a dial, a button, and so on.

Tilting the joy stick back and force and horizontally viewed from the examiner enables adjusting back-and-forth and horizontal positional relations between the subject's eye E and the fundus camera body. Turning the dial enables adjusting the vertical positional relation between the subject's eye E and the fundus camera body as well as the imaging light amount. The light amount is also adjustable by using the button.

These functions achieved by the operation unit 29 may be changed under control of the central control unit 19. Further, a dial or button may be provided for each individual function.

The central control unit 19 stores a still image (captured by the image sensor 5) in the image memory 20 as a digital image.

The table information stored in the storage unit of the central control unit 19 will be described in detail below with reference to FIG. 2. The table information illustrated in FIG. 2A stores the infrared light reflectance of the optic papilla and the maximum light amount of imaging light to be radiated thereto. The value of the infrared light reflectance equals the ratio of the light amount of infrared light reflected by the optic papilla to the light amount of infrared light radiated by the infrared light source 14.

Commonly, the reflectance of the optic papilla differs for each subject's eye because of individual difference and pathological changes as well as the wavelength of incident light.

FIG. 2B is a graph illustrating the reflected light amount (or reflectance) when infrared light is radiated onto the fundus. FIG. 2C is a graph illustrating the reflected light amount (or reflectance) when visible light is radiated onto the fundus. Referring to FIGS. 2B and 2C, the position of the optic papilla is indicated by a circle. As illustrated in these graphs, the visible light reflectance of the optic papilla is higher than the infrared light reflectance thereof.

The ratio of the reflected light amount to the light amount emitted by the light source is employed as the reflectance value. The reflected light amount is assumed to be equal to the light amount received by the image sensor 5.

From these facts, whether there is a correlation between the infrared light reflectance and the visible light reflectance of the optic papilla is not obvious. Further, when there is a correlation, what correlation it has is not obvious. For example, there is possibly a subject whose optic papilla reflects much infrared light but does not reflect visible light that much, and a subject whose optic papilla reflects much visible light but does not reflect infrared light that much.

However, as a result of inspection on an association between fundus image and radiation light amount for many subjects, it has been found that there is a correlation between the infrared light reflectance and the visible light reflectance of the optic papilla. That is, a subject having a small infrared light reflectance also has a small visible light reflectance, and a subject having a large infrared light reflectance also has a large visible light reflectance, and therefore the visible light reflectance can be presumed from the infrared light reflectance. Aspects of the present invention have been devised based on this result.

Knowing the visible light reflectance of the optic papilla enables the examiner to determine the imaging light amount with which the optic papilla is not over-exposed. Overexposure occurs when the image sensor 5 receives light amount exceeding the receivable light amount. Therefore, checking the characteristics of the image sensor 5 enables determining the maximum light amount to be received by the image sensor 5, with which the optic papilla is not over-exposed. Thus, the examiner can determine the maximum imaging light amount based on the determined maximum light amount and reflectance.

However, the examiner can obtain this maximum light amount on an experimental basis without checking the characteristics of the image sensor 5. Specifically, the examiner may refer to fundus images captured by using a plurality of light amounts to check the maximum light amount with which the optic papilla is not over-exposed. The examiner may analyze a plurality of images to obtain the maximum light amount. Further, the examiner can illuminate the optic papilla with a correct light amount.

Referring to FIG. 2B, the fundus area other than the optic papilla do not have a large difference between the infrared light reflectance and the visible light reflectance. This means that there is a large difference in reflection characteristics for wavelength change between the optic papilla and other fundus areas. Therefore, the characteristics of the optic papilla cannot be immediately derived from the characteristics of the fundus.

Among the table information, the light amount radiated by the infrared light source 14 is obtained with reference to the information stored in the storage unit of the observation light source control unit 25 or the central control unit 19. The light amount of reflected light from the optic papilla can be acquired with reference to the value of an electrical signal output according to the light amount received by the image sensor 5.

The image sensor 5 receives reflected infrared light to capture a fundus image, and acquires the light amount of reflected light from the optic papilla based on the obtained fundus image. Since the optic papilla is the brightest portion in the fundus image, acquiring the maximum luminance value or maximum pixel value in the fundus image enables obtaining the light amount of reflected light from the optic papilla.

The ratio denoted in FIG. 2A may be the maximum pixel value divided by the light amount radiated by the infrared light source 14. The maximum luminance value or pixel value may be obtained after performing predetermined processing for eliminating noise from the fundus image.

Among the table information, the imaging light amount denotes the light amount to be emitted by the flash light source 12. The central control unit 19 transmits the imaging light amount to the imaging light source control unit 24. Based on a control value corresponding to the received imaging light amount, the imaging light source control unit 24 controls the flash light source 12 to emit visible light.

Processing performed by the fundus camera 100 will be described below with reference to the flow chart illustrated in FIG. 3.

In step S101, the infrared light source 14 emits infrared light. The infrared light emitted by the infrared light source 14 is condensed by the condenser lens 13 and passes through the dichroic mirror 10. Then, the light flux of the infrared light is limited in ring shape by the ring diaphragm 9. The infrared light flux limited by the ring diaphragm 9 passes through the lenses 8 and 7 and then once forms an image of the ring diaphragm 9 on the perforated mirror 6.

Then, the light flux forming the image of the ring diaphragm 9 is reflected along the optical axis L1 by the perforated mirror 6, passes through the object lens 1, and forms an image of the ring diaphragm 9 again in the vicinity of the pupil Ep of the subject's eye E, thus illuminating the fundus Er of the subject's eye E.

After being reflected and scattered by the fundus Er illuminated by the light radiated from the infrared light source 14 which emits steady light, the light flux exits the pupil Ep of the subject's eye E, passes through the object lens 1, the imaging diaphragm 2, the focal lens 3, and the imaging lens 4, and reaches the image sensor 5.

In step S102, the imaging unit 23 including the image sensor 5 receives infrared light that has reached the image sensor 5 to capture a fundus image. Specifically, each pixel of the image sensor 5 receives infrared light and outputs an electrical signal according to respective light amount received. The signal output from each pixel is converted into digital form by the A/D conversion element 15, and the converted digital data is stored in the memory 16 as fundus image data.

The signal output from the image sensor 5 is converted into digital form by the A/D conversion element 15 and then output to a monitor 21 via the imaging control unit 22. The fundus image data stored in the memory 16 may be displayed on the monitor 21. In step S103, the monitor 21 displays a fundus observation image.

The examiner adjusts the light amount of the infrared light source 14 by using the operation unit 29 so that the fundus image is displayed on the monitor 21 with suitable luminance, and performs position adjustment for the optical unit of the fundus camera 100 relative to the subject's eye E by using an operation stick (not illustrated).

Then, the examiner operates a focus knob (not illustrated) to adjust the position of the optical axis direction of the focal lens 3, thus performing focus adjustment for the displayed fundus image. The operation unit 29 enables the examiner to manually adjust not only the light amount of the infrared light source 14 but also the light amount of the flash light source 12.

In step S104, the light metering value calculation unit 18 calculates the light amount of reflected light from the optic papilla. Specifically, the light metering value calculation unit 18 extracts the maximum pixel value among fundus areas from the fundus image data captured by the imaging unit 23 and stored in the memory 16, and acquires the maximum pixel value as a light metering value of the light amount of reflected light from the optic papilla.

In step S105, based on the infrared light amount metering value calculated by the light metering value calculation unit 18 and the infrared light amount value radiated by the infrared light source 14 under control of the observation light source control unit 25, the light emission amount calculation unit 26 calculates the ratio of the light amount of reflected light from the optic papilla to the light amount of infrared light radiated onto the subject's eye E.

The light emission amount calculation unit 26 acquires the maximum imaging light amount with reference to the table information about an association between the infrared light reflectance and the maximum imaging light amount with which the optic papilla is not over-exposed. The light emission amount calculation unit 26 transmits the determined maximum imaging light amount to the imaging light source control unit 24.

In step S106, the imaging light source control unit 24 controls the flash light source 12 to radiate visible light having the determined light amount onto the subject's eye E. The light flux emitted from the flash light source 12 is condensed by the condenser lens 11 and then reflected by the dichroic mirror 10. Then, the light flux is limited in ring shape by the ring diaphragm 9.

The visible light flux limited by the ring diaphragm 9 passes through the lenses 8 and 7, and then once forms an image of the ring diaphragm 9 on the perforated mirror 6. Then, the visible light is reflected along the optical axis L1 by the perforated mirror 6, passes through the object lens 1, and forms an image of the ring diaphragm 9 again in the vicinity of the pupil Ep of the subject's eye E, thus illuminating the pupil Ep of the subject's eye E.

In step S107, the imaging unit 23 drives the image sensor 5 at a timing of visible light radiation to capture a fundus image. After being reflected and scattered by the fundus Er illuminated by the light flux radiated from the infrared light source 12 which emits steady light, the light flux exists the pupil Ep of the subject's eye E, passes through the object lens 1, the imaging diaphragm 2, the focal lens 3, and the imaging lens 4, and reaches the image sensor 5.

The image sensor 5 receives visible light and generates an electronic signal. The A/D conversion element 15 converts the signal into digital form. The central control unit 19 stores the converted digital signal in the image memory 20 as still image data.

The above-mentioned processing enables the examiner to obtain an image with which the area of the optic papilla is not over-exposed, without performing light amount adjustment. Since the optic papilla has a higher visible light reflectance than other fundus areas, the light amount radiated onto the fundus area other than the optic papilla can be maximized by using the above-mentioned maximum imaging light amount.

Thus, the image quality of other fundus areas can be improved in the captured image. Since reflected infrared light radiated onto the subject's eye E is used, the examiner can determine the light amount of visible light (imaging light) and obtain a fundus image without causing myosis of the subject's eye E.

Although, in the present exemplary embodiment, the maximum imaging light amount is stored in the table information, the application of the present invention is not limited thereto. A correct light amount value may be prestored in the table information. The correct light amount value refers to a value set by the examiner when creating the table information.

In this case, the imaging light source control unit 24 controls the flash light source 12 to radiate onto the subject's eye E visible light having the correct light amount calculated by the light emission amount calculation unit 26. A fundus image obtained with the correct light amount in this way is useful for in-depth inspection of optic papilla conditions.

With a fundus camera according to a second exemplary embodiment, the imaging light source control unit 24 controls the flash light source 12 to radiate onto the subject's eye E visible light having a light amount corresponding to an exposure level of the optic papilla selected by the user on the operation unit 29. This makes it possible to obtain a fundus image at a desired exposure level selected by the user.

A configuration of an ophthalmologic imaging apparatus according to the present exemplary embodiment will be described below. The operation unit 29 of the fundus camera 100 is provided with a plurality of switches. When the user presses any one of the switches, the central control unit 19 outputs a signal denoting the pressed switch.

The storage unit (not illustrated) of the central control unit 19 stores, in association with each switch, information about the exposure level corresponding to the maximum light amount with which the optic papilla is not over-exposed in a fundus image captured with visible light, and information about the exposure level set as a correct level on a diagnostic basis. Upon reception of the signal from the central control unit 19, the control selection unit 28 acquires the information about the exposure level for a relevant switch from the storage unit of the central control unit 19.

The storage unit of the central control unit 19 has information about an association between the infrared light reflectance and the visible light reflectance of the optic papilla. This information may be table information about an association between the two reflectances or a function represented by predetermined parameters. In the present exemplary embodiment, the ratio of the light amount of reflected light received by the image sensor 5 to the light amount emitted from the light source is employed as the reflectance value.

The light metering value calculation unit 18 calculates the light amount of reflected light from the optic papilla. The light emission amount calculation unit 26 calculates the reflected light amount divided by the light amount of infrared light emitted from the infrared light source 14, and sets the resultant value as the infrared light reflectance of the optic papilla.

Based on this infrared light reflectance and the information about an association between the two reflectances stored in the storage unit of the central control unit 19, the light emission amount calculation unit 26 obtains the visible light reflectance of the optic papilla. Since the light amount to be received by the image sensor 5 is determined by the information about the exposure level acquired by the control selection unit 28, the light emission amount calculation unit 26 calculates the light amount of visible light to be emitted from the flash light source 12 based on the light amount to be received by the image sensor 5 and the visible light reflectance.

The imaging light source control unit 24 controls the flash light source 12 to emit the calculated light amount.

As mentioned above, the present exemplary embodiment can control the imaging light amount so as to achieve an exposure level desired by the user based on the infrared light reflectance of the optic papilla, thus obtaining a fundus image desired by the user.

Controlling the light amount not to over-expose the optic papilla in a fundus image in this way enables not only preventing information loss due to overexposure but also increasing the light amount to be radiated onto the fundus area other than the optic papilla. This improves the image quality of the fundus area other than the optic papilla and facilitates the examiner correcting an obtained fundus image through image processing. Further, radiating the light amount with which the optic papilla is to be correctly exposed makes it easier to locate a pathological change appearing on the optic papilla in the obtained fundus image.

A third exemplary embodiment includes the light amount control selection unit 28 which selects either one of a first exposure control mode for radiating the imaging light amount with which the optic papilla is to be correctly exposed in a captured image and a second exposure control mode for radiating the imaging light amount with which the fundus area other than the optic papilla is to be correctly exposed therein. The examiner can select either mode depending on situation. The configuration of the fundus camera is similar to that described in the first exemplary embodiment and therefore duplicated descriptions will be omitted.

The present exemplary embodiment stores a function for determining the imaging light amount with which the fundus area other than the optic papilla is correctly exposed. This function is a linear function for calculating the imaging light amount with which the fundus area other than the optic papilla is correctly exposed from the infrared light reflectance for the entire fundus area.

Similar to the table information described in the first exemplary embodiment, because of a difference between the observation light source wavelength and the imaging light source wavelength, this function is determined based mainly on the reflection wavelength characteristics of the human fundus and the reflective wavelength characteristics of the optic papilla.

Figure 4:
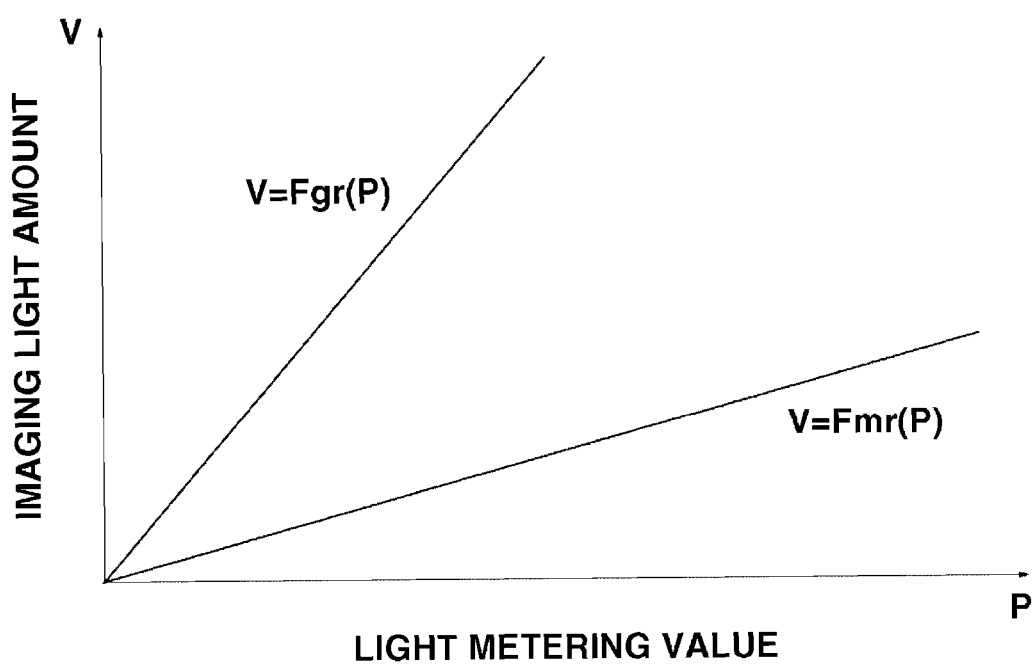
FIG. 4 is graph illustrating an association between the reflection intensity and the imaging light amount according to a second exemplary embodiment.

FIG. 4 is a graph illustrating the function. The horizontal axis is assigned the ratio P of the infrared light amount metering value to the light amount emitted from the infrared light source 14, and the vertical axis is assigned an imaging light amount V. A graph Fmr (P) illustrates a correct light amount to be radiated onto the optic papilla, and a graph Fgr (P) illustrates a light amount to be radiated onto the entire fundus.

Figure 5:
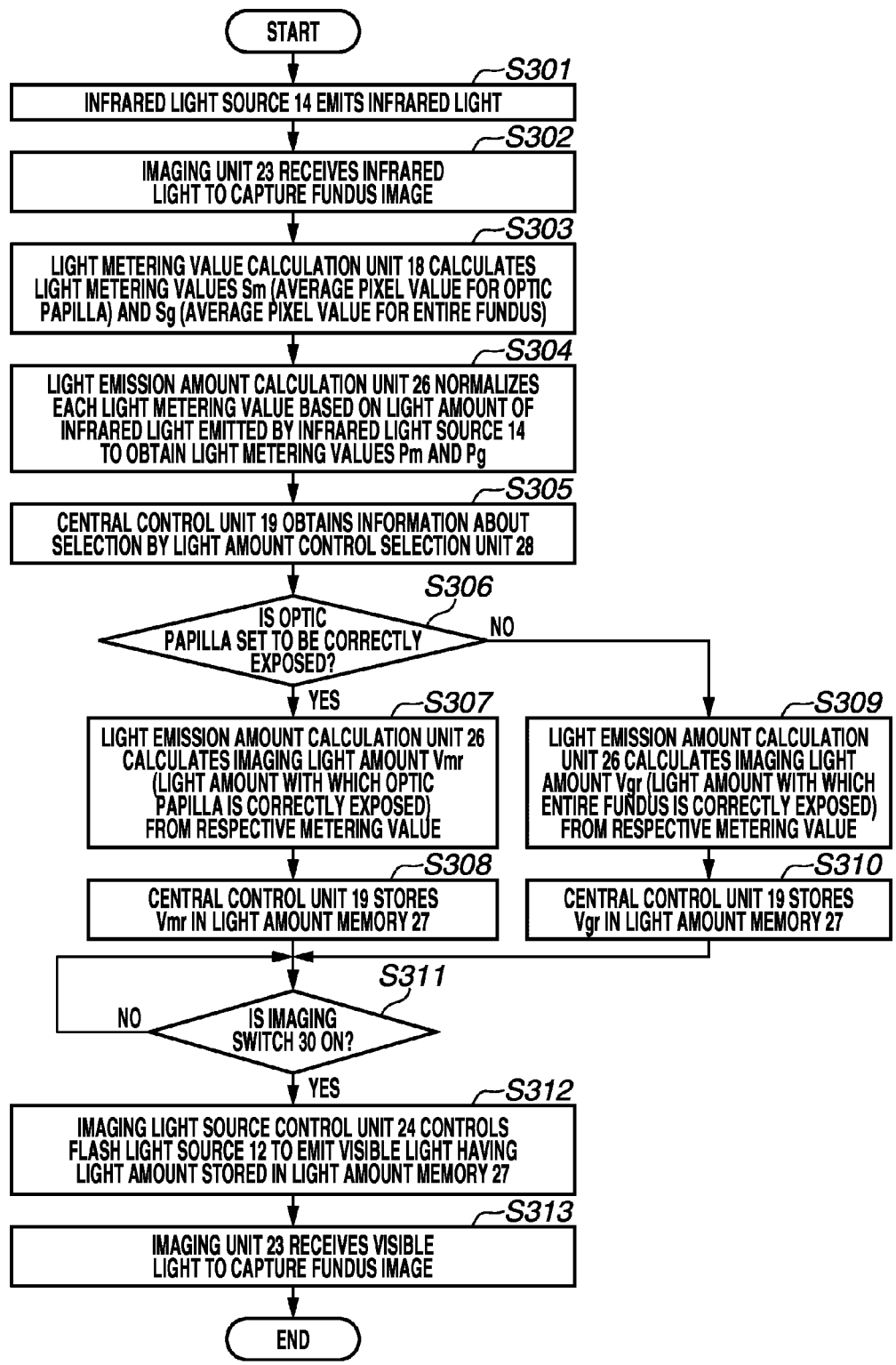
FIG. 5 is a flow chart illustrating processing performed by a fundus camera according to a third exemplary embodiment.

Processing performed by the fundus camera according to the present exemplary embodiment will be described below with reference to FIG. 5.

In step S301, the infrared light source 14 emits infrared light. The infrared light emitted by the infrared light source 14 illuminates the pupil Ep of the subject's eye E via the fundus illumination optical system.

In step S302, the image sensor 5 receives infrared light reflected by the fundus to capture a fundus image. A signal output from each pixel is converted into digital form by the A/D conversion element 15, and the converted digital data is temporarily stored in the memory 16.

The light metering value calculation unit 18 calculates a light metering value Sg (an average pixel value for the entire fundus) from the pixel output data stored in the memory 16. Although the light metering value Sg includes pixel output data from the optic papilla, because of average processing, the value Sg is employed as a value representing the light amount of reflected light from the fundus area other than the optic papilla. The average pixel value may be calculated with pixel output from other than the optic papilla.

In step S303, the light metering value calculation unit 18 also calculates a light metering value Sm (an average pixel value for the optic papilla) detected by the optic papilla position detection unit 17, and outputs these calculated light metering values to the light emission amount calculation unit 26.

Based on these light metering values, the light emission amount calculation unit 26 determines the imaging light amount with reference to the function stored in the storage unit of the central control unit 19. Since the above-mentioned light metering values Sg and Sm are affected by the observation light amount during light metering, the light emission amount calculation unit 26 normalizes the light metering values Sg and Sm by using the observation light amount based on the control state of the observation light source control unit 25.

In step S304, the light emission amount calculation unit 26 performs normalization by dividing the light metering values Sg and Sm by the light amount of infrared light emitted by the infrared light source 14. After normalization, a light metering value Pg for the entire fundus and a light metering value Pm for the optic papilla are obtained. The light metering value Pg denotes the infrared light reflectance of the entire fundus area, and the light metering value Pmg denotes the infrared light reflectance of the optic papilla.

In step S305, the light amount control selection unit 28 receives from the examiner a selection of either one of two exposure control modes (one mode gives priority to the image quality of the optic papilla and the other mode gives priority to the image quality of the entire fundus), and selects either mode according to the selection. When a selection is not input, the exposure control mode for giving priority to the image quality of the entire fundus is assumed as a default value.

In step S306, the central control unit 19 determines which exposure control mode is selected (which portion is to be given priority) by the light amount control selection unit 28. When the light amount control selection unit 28 selects the first exposure control mode for correctly exposing the optic papilla (YES in step S306), the processing proceeds to step S307. In step S307, the light emission amount calculation unit 26 calculates an imaging light amount Vmr=Fmr (Pm) from the light metering value Pm representing the light amount of reflected infrared light from the optic papilla. In step S308, the central control unit 19 stores the light metering value Vmr in the light amount memory 27 as a first visible light amount.

Otherwise, when the light amount control selection unit 28 selects the second exposure control mode for correctly exposing the entire fundus (No in step S306), the processing proceeds to step S309. In step S309, the light emission amount calculation unit 26 calculates an imaging light amount Vgr with which the fundus image is correctly exposed, based on the light metering value Pg (an average light amount of reflected observation light from the entire fundus). In step S310, the central control unit 19 stores the imaging light amount Vgr in the light amount memory 27 as a second visible light amount.

Upon completion of position and focus adjustments, the examiner presses the imaging switch 30 (YES in step S311), and the processing proceeds to step S312. In step S312, the central control unit 19 instructs the imaging light source control unit 24 to control the flash light source 12 to emit pulsed light to capture an image by using the latest light amount out of imaging light amounts stored in the light amount memory 27.

In step S313, the image sensor 5 of the imaging unit 23 receives visible light, emitted from the flash light source 12 and reflected by the fundus, to obtain image data, thus capturing a fundus image. The central control unit 19 stores the image data obtained by the image sensor 5 in the image memory 20.

The present exemplary embodiment enables selecting which of the optic papilla and the entire fundus is to be correctly exposed in this way and suitably controls the light amount according to the selection. Therefore, a desired image can be obtained while remarkably saving time and labor for light amount adjustment.

A fourth exemplary embodiment performs processing for preventing overexposure of the optic papilla in a fundus image and reduction in signal-to-noise (S/N) ratio of image in selection of the exposure control mode in the third exemplary embodiment.

Figure 6:
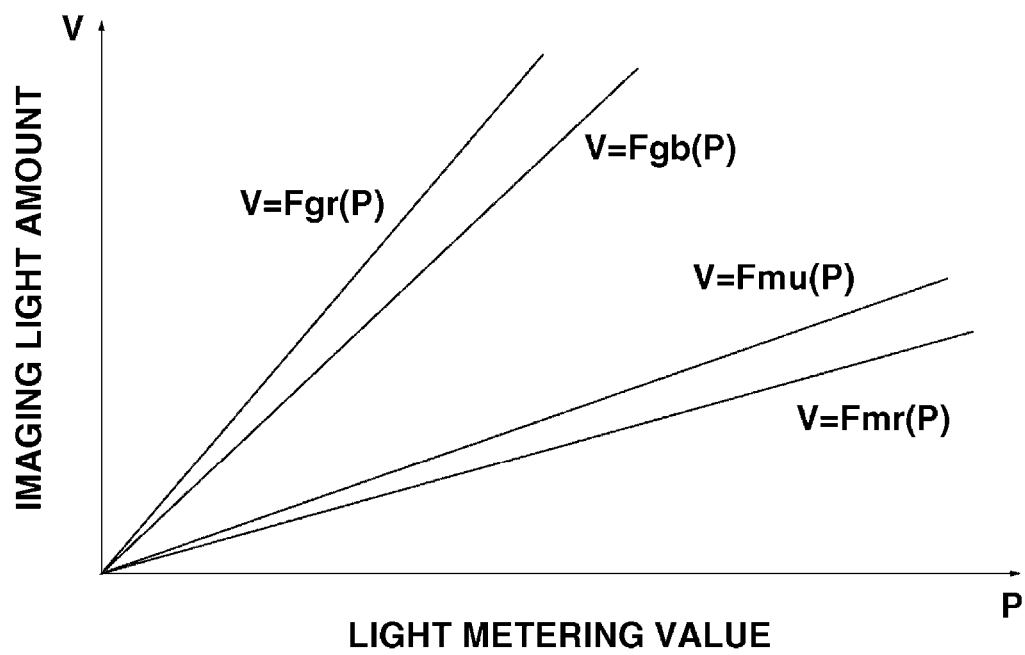
FIG. 6 is graph illustrating an association between the reflection intensity and the imaging light amount according to a fourth exemplary embodiment.

FIG. 6 is a graph illustrating a function. The vertical axis is assigned the ratio P of the infrared light amount metering value to the light amount emitted from the infrared light source 14, and the horizontal axis is assigned the imaging light amount V. A graph Fmr (P) illustrates a correct light amount to be radiated onto the optic papilla, and a graph Fmu (P) illustrates a maximum light amount to be radiated thereto. A graph Fgb (P) illustrates a minimum light amount to be radiated onto the entire fundus, and a graph Fgr (P) illustrates a correct light amount to be radiated thereto.

Referring to FIG. 6, although the graphs are illustrated as linear functions, each function does not necessarily a linear function depending on the wavelength of light to be radiated onto the subject's eye E.

Figure 7:
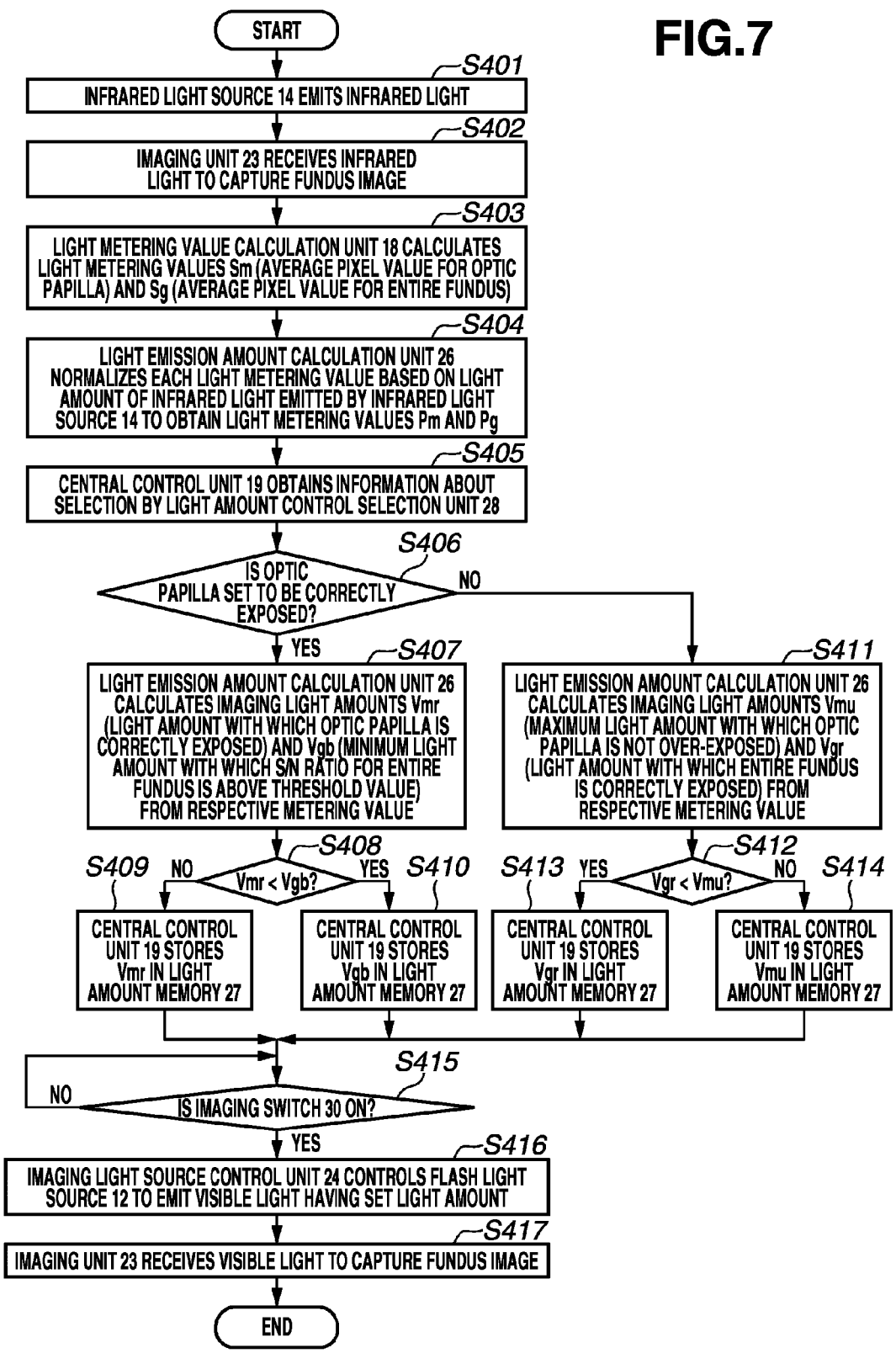
FIG. 7 is a flow chart illustrating processing performed by a fundus camera according to the fourth exemplary embodiment.

Processing performed by a fundus camera according to the present exemplary embodiment will be described below with reference to FIG. 7. Duplicated descriptions will be omitted for processing similar to the third exemplary embodiment illustrated in FIG. 5.

Light amount control processing according to the present exemplary embodiment controls the light amount firstly in consideration of preventing reduction in total amount of image information and secondly in consideration of correctly exposing the optic papilla or the entire fundus selected.

In step S406, the central control unit 19 determines which exposure control mode is selected (which portion is to be given priority) by the light amount control selection unit 28. When the light amount control selection unit 28 selects the first exposure control mode for correctly exposing the optic papilla (YES in step S406), the processing proceeds to step S407. In step S407, the light emission amount calculation unit 26 calculates an imaging light amount Vmr=Fmr (Pm) from the light metering value Pm representing the light amount of reflected infrared light from the optic papilla.

As mentioned above, the optic papilla commonly has a remarkably high reflectance in comparison with other fundus area. In this case, the imaging light amount Vmr with which the optic papilla is correctly exposed and the imaging light amount Vgr with which the entire fundus is correctly exposed have a relation Vmr<Vgr. Therefore, when a fundus image is captured with the imaging light amount Vmr, the fundus area other than the optic papilla may be under-exposed, possibly resulting in reduced S/N ratio for the fundus area other than the optic papilla.

Accordingly, based on the light metering value Pg (an average light amount of reflected observation light from the entire fundus), the light emission amount calculation unit 26 calculates a minimum imaging light amount Vgb=Fgb (Pg) that does not fall below a threshold value defined by the S/N ratio for the fundus area other than the optic papilla.

Figure 8A:
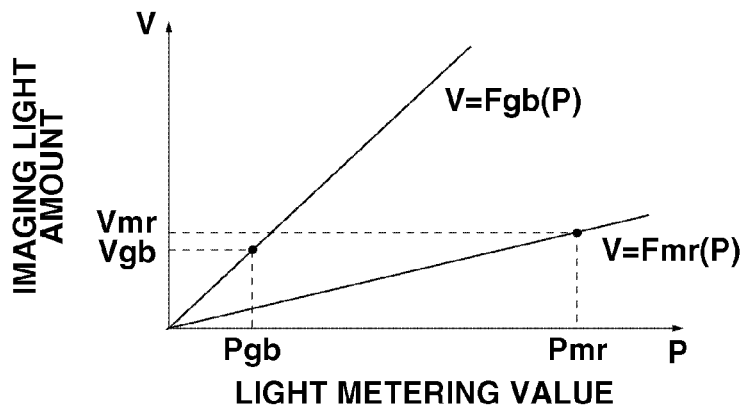
FIGS. 8A, 8B, 8C, and 8D illustrate relations between the imaging light amount and the light metering values.

In step S408, the light emission amount calculation unit 26 compares the imaging light amount Vmr with the imaging light amount Vgb. When Vmr>Vgb is determined as illustrated in FIG. 8A (NO in step S408), the processing proceeds to step S409. In step S409, the central control unit 19 stores the imaging light amount Vmr in the light amount memory 27.

Figure 8B:
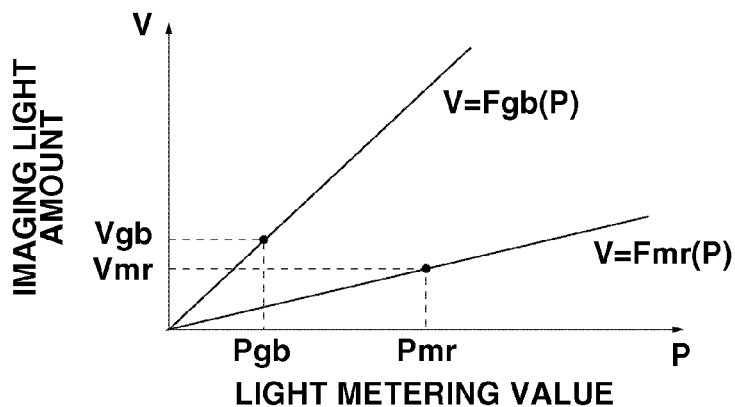

Otherwise, when Vmr<Vgb is determined as illustrated in FIG. 8B (YES in step S408), the processing proceeds to step S410. In step S410, the central control unit 19 stores the imaging light amount Vgb in the light amount memory 27, giving higher priority to preventing loss of information about the fundus area other than the optic papilla than to correctly exposing the optic papilla.

When the second exposure control mode for correctly exposing the entire fundus is selected (NO in step S406), the processing proceeds to step S411. In step S411, based on the light metering value Pg (an average light amount of reflected observation light from the entire fundus), the light emission amount calculation unit 26 calculates an imaging light amount Vgr with which the fundus image is correctly exposed.

Based on the light metering value Pm (a value of reflected observation light from the optic papilla), the light emission amount calculation unit 26 calculates an imaging light amount Vmu with which the optic papilla is over-exposed, and sets the resultant value as a maximum imaging light amount.

Figure 8C:
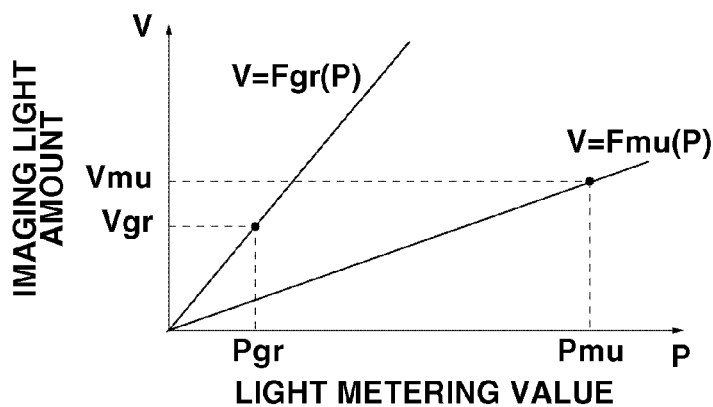

In step S412, the light emission amount calculation unit 26 compares the imaging light amount Vgr with the imaging light amount Vmu. When Vgr<Vmu is determined as illustrated in FIG. 8C (YES in step S412), the processing proceeds to step S413. In step S413, the central control unit 19 stores the imaging light amount Vgr in the light amount memory 27.

Figure 8D:
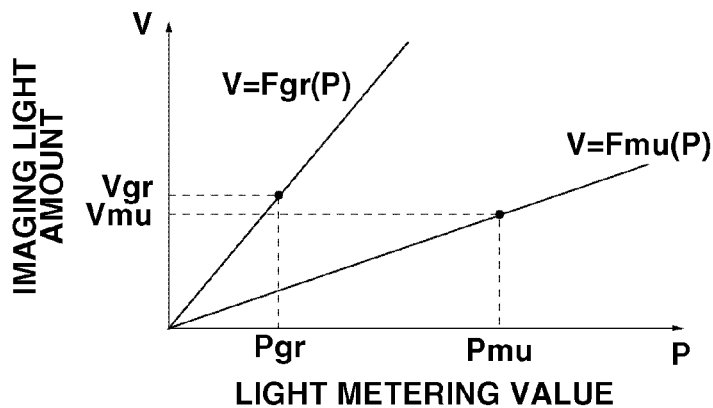

Otherwise, when Vgr>Vmu is determined as illustrated in FIG. 8D (NO in step S412), the processing proceeds to step S414. In step S414, the central control unit 19 stores the imaging light amount Vmu in the light amount memory 27, giving higher priority to preventing the optic papilla from being over-exposed than to correctly exposing the entire fundus. This aims at preventing the amount of image information from remarkably decreasing when the optic papilla is over-exposed.

The present exemplary embodiment enables selecting which of the optic papilla and the entire fundus is to be correctly exposed in this way and suitably controls the light amount according to the selection. Therefore, a desired image can be obtained while remarkably saving time and labor for light amount adjustment.

In the exposure control mode for correctly exposing the optic papilla, when the S/N ratio of the fundus falls below a permissible value, the minimum light amount with which the S/N ratio of the fundus does not fall below the permissible value is set as the imaging light amount, thus preventing reduction in amount of information caused by reduced S/N ratio.

In the exposure control mode for correctly exposing the entire fundus, when the optic papilla is over-exposed, the maximum light amount with which the optic papilla is not over-exposed is set as the imaging light amount, thus preventing loss of information about the optic papilla.

Exposure control is not limited thereto but may be performed so that the examiner selects which of the image quality of the optic papilla and the image quality of the fundus area other than the optic papilla is given priority. In this case, when either the optic papilla or other fundus area is selected, over-exposure of image may occur when the optic papilla is over-exposed or the S/N ratio of the entire fundus may fall below a permissible value. However, it is useful for in-depth inspection of either the optic papilla or other fundus areas.

With the fundus camera according to the forth exemplary embodiment, it is possible to select which of the optic papilla and the fundus area other than the optic papilla is given priority, enabling the examiner to obtain a desired fundus image depending on situation.

With a fundus camera according to a fifth exemplary embodiment, the imaging unit 23 includes the optic papilla position detection unit 17 which detects the position of the optic papilla from a fundus image. The optic papilla position detection unit 17 detects the area of the optic papilla from a fundus image and acquires the pixel value of the area as the light amount of reflected light from the optic papilla.

Although the maximum luminance value or pixel value of the fundus image acquired by receiving infrared light is used in the above-mentioned exemplary embodiments, incorrect detection due to noise may occur. Detecting the position of the optic papilla enables correctly detecting the light amount of reflected light from the optic papilla.

The optic papilla position detection unit 17 included in the imaging unit 23 detects the position of the optic papilla based on pixel output data of the image sensor 5 stored in the memory 16. The optic papilla position detection unit 17 is not necessarily be included in the imaging unit 23 but may be connected with the central control unit 19.

Figure 9:
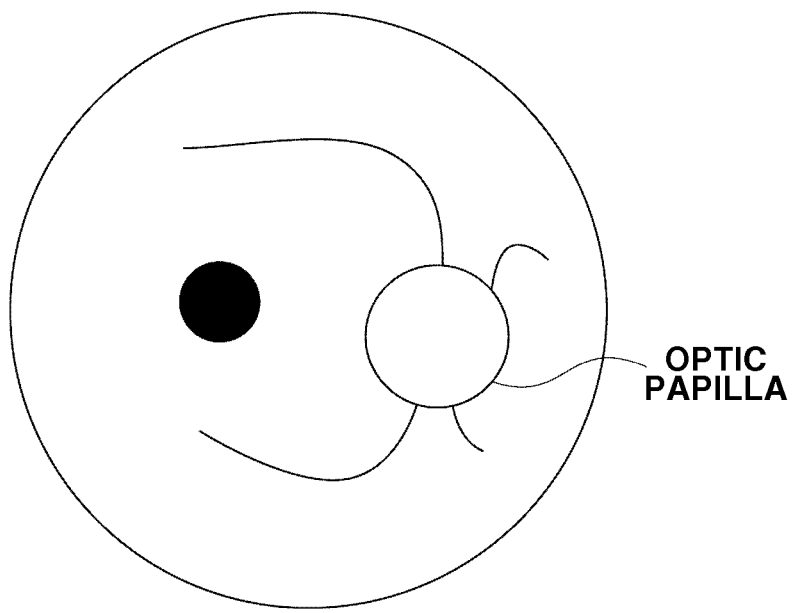
FIG. 9 illustrates an exemplary fundus image.

FIG. 9 illustrates an exemplary common fundus image. Since the optic papilla portion is commonly the brightest portion in the fundus image, the optic papilla position detection unit 17 recognizes a portion having a pixel value of 200 or more, for example, as a candidate of optic papilla portion.

The optic papilla position detection unit 17 also takes the size and shape into consideration. Although there is individual difference, the optic papilla is commonly said to have an area of 0.8 to 6 $mm^2$. It has an approximately elliptic shape.

In the present exemplary embodiment, the optic papilla position detection unit 17 recognizes a continuous portion having a pixel value equal to or greater than a predetermined value, an area of 0.4 $mm^2$ or more, and an approximately elliptic shape as the optic papilla, and detects its position and range. When the optic papilla position detection unit 17 can detect the position of the optic papilla in the fundus area, it outputs the position information to the light metering value calculation unit 18.

The light metering value calculation unit 18 acquires the pixel value of the optic papilla by using an average value, a median, and a maximum value excluding higher several percents. Detection of the optic papilla is not limited thereto but may be performed through comparison with peripheral pixel values.

Figure 10:
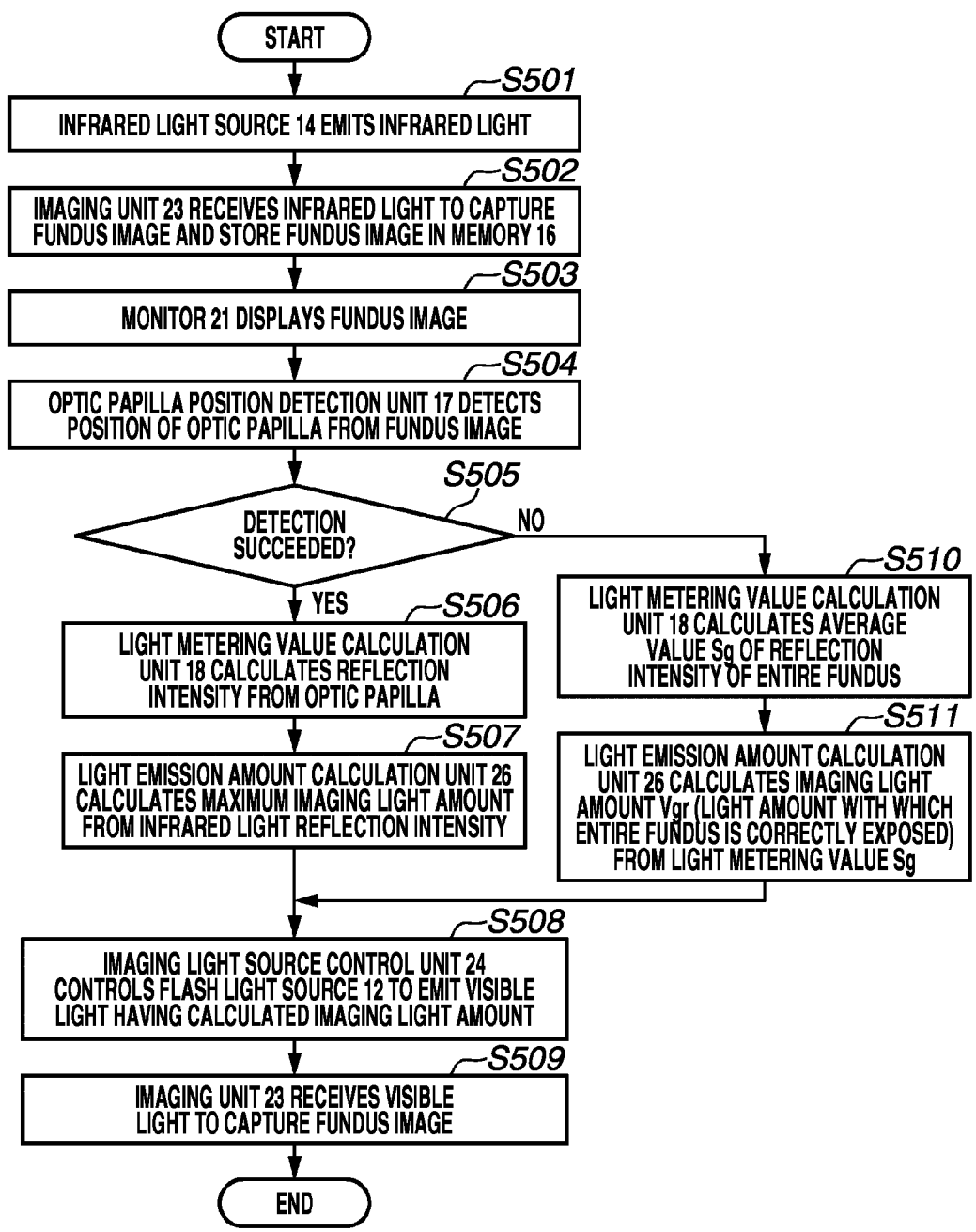
FIG. 10 is a flow chart illustrating processing performed by a fundus camera according to a fifth exemplary embodiment.

Processing performed by the fundus camera according to the fifth exemplary embodiment will be described below with reference to FIG. 10. Duplicated descriptions will be omitted for processing similar to the first exemplary embodiment.

In step S505, the central control unit 19 determines whether detection of the optic papilla succeeds. When detection of the optic papilla succeeds (YES in step S505), the processing proceeds to step S506.

When detection of the optic papilla fails (NO in step S505), the processing proceeds to step S510. In step S510, the light metering value calculation unit 18 calculates the light amount for the entire fundus. Specifically, the light metering value calculation unit 18 calculates an average light amount of reflected infrared light from the entire fundus based on the fundus image data to calculate a light metering value Sg.

In step S511, the light emission amount calculation unit 26 normalizes the light metering value Sg by using the light amount emitted by the infrared light source 14 during measurement to calculate a light metering value Pg, and calculates a light amount Vgr with which the entire fundus is correctly exposed, with reference to the function stored in the storage unit of the central control unit 19. The central control unit 19 stores the light amount Vgr in the light amount memory 27 as the imaging light amount.

When the optic papilla cannot be detected, imaging is automatically performed by using the imaging light amount for the entire fundus, facilitating setting before imaging. Since the position of the optic papilla is detected from an image to calculate the light amount of reflected light from the optic papilla, incorrect detection due to noise can be prevented and the light amount can be correctly controlled.

Detection of the optic papilla position which is characteristic processing of the present exemplary embodiment may be applied to the fundus camera according to any one of the second to fourth exemplary embodiments. In this case, similar to the fifth exemplary embodiment, the optic papilla position detection unit 17 is preferably provided.

With a fundus camera according to a sixth exemplary embodiment, the storage unit of the central control unit 19 includes table information for obtaining a maximum imaging light amount, a correct light amount, and a minimum imaging light amount. The maximum and minimum values are obtained based on the light amount of reflected infrared light from the entire fundus out of infrared light emitted from the infrared light source 14.

A range of light amount adjustable by the examiner on the operation unit 29 is limited to a range between the minimum and maximum values. Duplicated descriptions will be omitted for similar configuration of the fundus camera 100 according to the first exemplary embodiment.

The table information stored in the storage unit of the central control unit 19 stores the light amount emitted from the infrared light source 14, reflected by the optic papilla, and received by the image sensor 5, and a maximum imaging light amount, a preset correct imaging light amount, and a minimum imaging light amount corresponding to this light amount value.

The minimum imaging light amount refers to a light amount with which a S/N ratio of the image of the optic papilla preset by the examiner at the time of setting before imaging or at the time of manufacture of apparatus does not fall below a permissible value.

In the present exemplary embodiment, since the light amount of infrared light emitted from the infrared light source 14 is a fixed value, the light amount of infrared light received by the image sensor 5 is directly associated with the visible light amount in the table information. With reference to the table information, the central control unit 19 can suitably determine the imaging light amount with which the optic papilla in an image is not over-exposed and the S/N ratio is within the permissible range from the light amount of infrared light reflected by the optic papilla.

Figure 11:
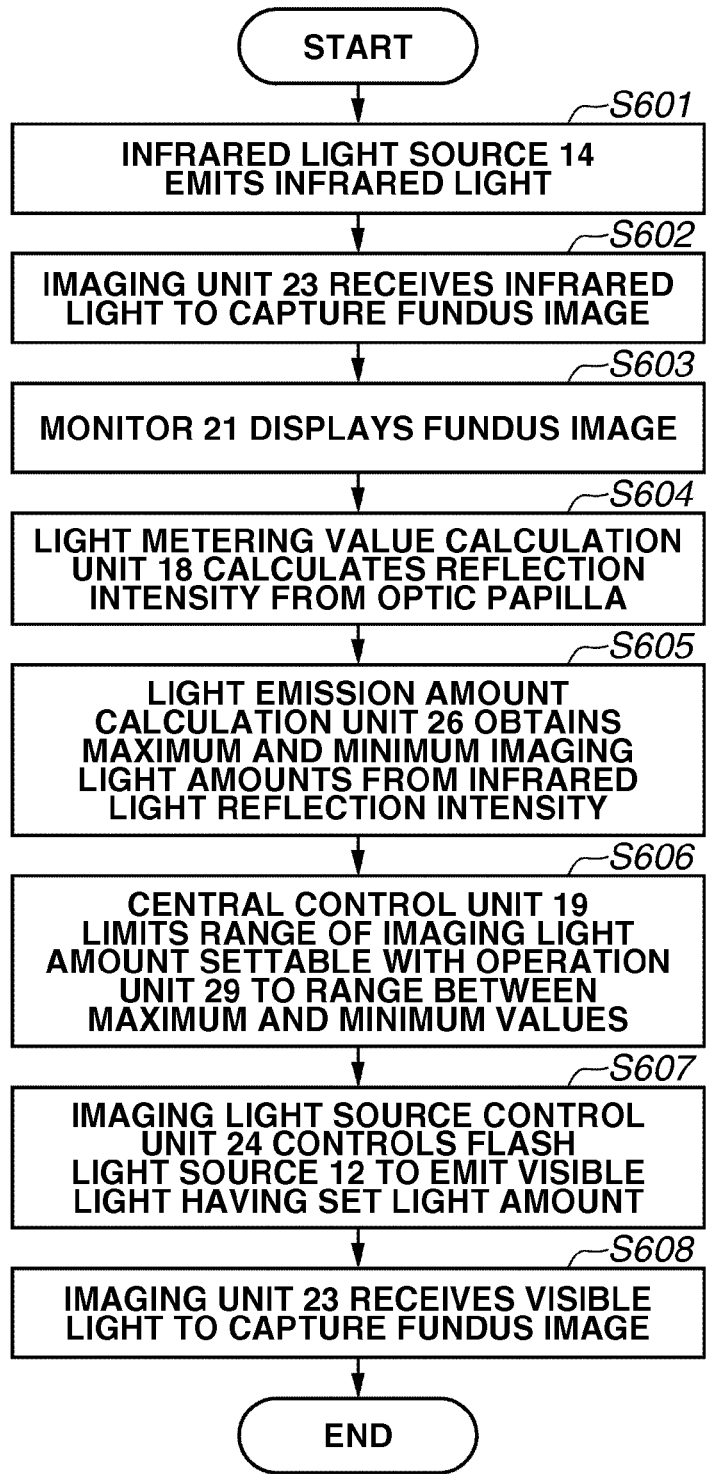
FIG. 11 is a flow chart illustrating processing performed by a fundus camera according to a sixth exemplary embodiment.

Processing performed by the fundus camera according to the present exemplary embodiment will be described below with reference to FIG. 11. Duplicated descriptions will be omitted for processing similar to the first exemplary embodiment.

In step S605, the light emission amount calculation unit 26 acquires the maximum and minimum imaging light amounts with reference to the table information about an association between the infrared light amount metering value obtained by the light metering value calculation unit 18 and the maximum imaging light amount with which the optic papilla is not over-exposed. Based on the acquired maximum and minimum values, the central control unit 19 sets a range of light amount to be emitted by the flash light source 12. This control can limit the light amount adjustable by the examiner on the operation unit 29.

When the operation unit 29 is provided with a dial, the range of light amount can be limited by limiting the movable range of the dial or decreasing the ratio of change in imaging light amount to the amount of rotation of the dial. When the operation unit 29 is provided with a button for changing the light amount, the range of light amount changeable by using this button can be limited.

When the operation unit 29 is provided with a light amount increase button and a light amount decrease button, the range of light amount changeable by using the two buttons can be limited. Some of buttons respectively corresponding to a plurality of light amounts may be used.

As another example, when the examiner selects a light amount outside the set range of light amount on the operation unit 29, a warning may be displayed on the monitor 21 under control of the central control unit 19. In this case, the central control unit 19 and the monitor 21 constitute a warning means. The warning is not limited to be displayed but may be notified to the examiner by sound or LED indication.

In step S606, the imaging light source control unit 25 acquires a light amount value set by the examiner and controls the flash light source 12 to emit visible light having the set light amount.

Limiting in this way the range of imaging light amount adjustable on the operation unit 29 based on the light amount of reflected infrared light facilitates the examiner adjusting the light mount than in a case where the range is not limited.

The average light amount of reflected infrared light from the entire fundus may also be used to control the light amount of visible light (imaging light). This enables the examiner to set a correct imaging light amount in consideration of not only the optic papilla but also other fundus areas.

In this case, the storage unit of the central control unit 19 needs to store two different pieces of table information: table information A about an association between the light amount of reflected infrared light and the light amount of imaging light (visible light) on the optic papilla, and table information B about an association between the average light amount of reflected infrared light and the light amount of imaging light (visible light) on the fundus.

The table information A stores the ratio of the light amount of infrared light reflected by the optic papilla to the radiated infrared light amount, and a maximum visible light amount, a correct visible light amount, and a minimum visible light amount corresponding to the ratio. The table information B stores the ratio of the average light amount of infrared light reflected by the fundus to the radiated infrared light amount, and a maximum visible light amount, a correct visible light amount, and a minimum visible light amount corresponding to the ratio.

The imaging light amount is limited to a range corresponding to a logical multiplication (AND) set or logical addition (OR) set of the range of imaging light amount defined by the maximum and minimum values (obtained from the table information A) and the range of imaging light amount (obtained from the table information B).

The examiner can select a suitable light amount for the optic papilla and/or the entire fundus by selecting alight amount from the limited range.

Limitation of the range of imaging light amount selectable on the operation unit 29 is not limited to the above-mentioned exemplary embodiments. For example, the imaging light amount may be limited to a range corresponding to the logical addition (OR) set. In this case, the examiner can easily select an imaging light amount with which both the optic papilla and the entire fundus area are correctly illuminated.

Either a set of the maximum and the correct light amounts for the optic papilla or a set of the minimum and suitable imaging light amounts for the entire fundus may be selected by the examiner on the operation unit 29. In control by the imaging light source control unit 25, the imaging light amount adjustable by the examiner on the operation unit 29 may be limited to the maximum value or below without using the minimum value or to the minimum value or above without using the maximum value.

According to aspects of the present invention, not only the ratio of the received light amount to the radiated light amount but also many other values can be employed as the infrared light reflectance or visible light reflectance value. For example, when a fixed amount is used as the infrared light to be radiated onto the subject's eye E, the light amount of infrared light received by the image sensor 5 may be used.

According to aspects of the present invention, although the light amount is controlled by the emission time period during which visible light is emitted from the flash light source 12, the method for controlling the light amount is not limited thereto. The light amount can also be controlled by the intensity of light to be emitted from the flash light source 12 and the shutter speed, i.e., the time period during which the shutter is open.

Further, the light amount of visible light to be received by the image sensor 5 may be controlled by the combination of the light intensity and the shutter speed. In this case, the light emission amount calculation unit 26 determines the light amount of visible light to be received by the image sensor 5, and sets the intensity of light from the flash light source 12, a time period for light emission, and a shutter speed which are necessary to receives the determined light amount. Aspects of the present invention may be attained, for example, by referring to stored table information about an association between the light intensity, a time period for light emission, and a shutter speed.

Aspects of the present invention may be attained also by performing the following processing. Specifically, software program for implementing some functions of the above-mentioned exemplary embodiments is supplied to a system or apparatus via a network or various storage media, and a computer (or CPU or microprocessor unit (MPU)) of the system or apparatus loads and executes the software program.

In this case, a program for executing a part of processing illustrated in FIGS. 3, 5, 7, 10, and 11 according to the above-mentioned exemplary embodiments is stored in the storage unit of the central control unit 19. Then, the program is loaded into a random access memory (RAM) of the central control unit 19, and the CPU of the central control unit 19 reads and executes the program.

Aspects of the present invention have been devised based on a finding of a correlation between the amplitude of the infrared light reflected by the optic papilla and the amplitude of the visible light reflected thereby. Utilizing this correlation makes it possible to control the light amount of imaging light (visible light) based on the light amount of infrared light reflected by the optic papilla, thus enabling the optic papilla to be exposed to a desired light amount while preventing myosis of the subject's eye.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-059430 filed Mar. 16, 2010, which is hereby incorporated by reference herein in its entirety.

What is claimed is:

1. An ophthalmologic imaging apparatus comprising:
   a control unit configured to control, based on a pixel value of the optic papilla in an infrared light image of the fundus of a subject's eye to which infrared light is radiated, the light amount of visible light to be radiated onto the subject's eye; and
   an imaging unit configured to capture an image of the fundus of the subject's eye to which visible light having the controlled light amount is radiated.

2. The ophthalmologic imaging apparatus according to claim 1, wherein the control unit controls the light amount of visible light to be radiated onto the subject's eye with reference to information about an association between a ratio of the pixel value to the light amount of infrared light radiated and the visible light amount with which the fundus of the subject's eye is subjected to a predetermined exposure level.

3. The ophthalmologic imaging apparatus according to claim 2, wherein the information about the association is generated by using a correlation between the infrared light reflectance and the visible light reflectance of the optic papilla.

4. The ophthalmologic imaging apparatus according to claim 2, wherein the visible light amount with which the fundus of the subject's eye is subjected to a predetermined exposure level is a maximum light amount with which the optic papilla is not over-exposed in a fundus image captured by the imaging unit; and
   wherein the control unit controls the light amount of visible light to be radiated onto the subject's eye to become the maximum light amount.

5. The ophthalmologic imaging apparatus according to claim 2, wherein the visible light amount with which the fundus of the subject's eye is subjected to a predetermined exposure level is a set visible light amount with which the optic papilla is correctly exposed in the fundus image captured by the imaging unit, and
   wherein the control unit controls the visible light amount to radiate visible light having the set light amount onto the subject's eye.

6. The ophthalmologic imaging apparatus according to claim 1, further comprising:
   a selection unit configured to select an exposure level of the optic papilla,
   wherein the control unit controls a visible light source to radiate onto the subject's eye visible light having a light amount corresponding to the selected exposure level.

7. The ophthalmologic imaging apparatus according to claim 1, further comprising:
   a light amount acquisition unit configured to acquire a first visible light amount with which the fundus of the subject's eye is subjected to a first exposure level based on the light amount of reflected infrared light from the optic papilla out of infrared light radiated onto the subject's eye, and a second visible light amount with which the fundus of the subject's eye is subjected to a second exposure level based on the light amount of reflected infrared light from the fundus area other than the optic papilla out of infrared light radiated onto the subject's eye,
   wherein the control unit controls the light amount of visible light to be radiated onto the subject's eye based on the light amount acquired by the light amount acquisition unit.

8. The ophthalmologic imaging apparatus according to claim 7, further comprising:
   another selection unit configured to select either one of the first and second exposure levels.

9. The ophthalmologic imaging apparatus according to claim 7, wherein the first visible light amount is the maximum light amount with which the optic papilla is not over-exposed in the captured fundus image, and
   wherein, when the second visible light amount is greater than the first visible light amount, the control unit controls a visible light source to radiate visible light having the first visible light amount.

10. The ophthalmologic imaging apparatus according to claim 7, wherein the second visible light amount is a minimum light amount with which the image quality of the captured fundus image does not fall below a threshold value, and
    wherein, when the first visible light amount is smaller than the second visible light amount, the control unit controls a visible light source to radiate visible light having the second visible light amount.

11. The ophthalmologic imaging apparatus according to claim 7, further comprising:
    an operation unit configured to enable an examiner to adjust the light amount,
    wherein the first visible light amount is the maximum light amount with which the optic papilla is not over-exposed in the captured fundus image,
    wherein the second visible light amount is the minimum light amount with which the image quality of the captured fundus image does not fall below a threshold value, and
    wherein the control unit controls a range of light amount adjustable on the operation unit based on the first and second visible light amounts.

12. The ophthalmologic imaging apparatus according to claim 1, further comprising:
    a detection unit configured to detect a predetermined area as the optic papilla based on the pixel value in the infrared light image; and an acquisition unit configured to acquire a pixel value of the optic papilla based on the pixel value of the detected area.

13. The ophthalmologic imaging apparatus according to claim 1, further comprising:
an operation unit configured to enable an examiner to adjust the light amount,
wherein the control unit controls a range of light amount adjustable on the operation unit based on the pixel value in the infrared light image of the subject's eye to which infrared light is radiated.

14. The ophthalmologic imaging apparatus according to claim 1, further comprising:
an operation unit configured to enable an examiner to adjust the light amount,
wherein the control unit sets a range of light amount adjustable on the operation unit based on the pixel value in the infrared light image of the subject's eye to which infrared light is radiated, and
wherein the control unit includes a warning unit configured to output a warning when a light amount outside the set range is selected.

15. The ophthalmologic imaging apparatus according to claim 1, wherein the control unit controls at least one of the intensity of light to be emitted by a visible light source, a time period for light emission, and a shutter speed to adjust the light amount of visible light to be radiated onto the subject's eye and received by an image sensor via the fundus of the subject's eye.

16. The ophthalmologic imaging apparatus according to claim 1, further comprising:
an imaging unit configured to receive infrared light and visible light to obtain image data from an electrical signal corresponding to the received light amount;
an infrared light source configured to emit infrared light;
a visible light source configured to emit visible light;
an illumination optical system configured to guide the emitted infrared light and the emitted visible light to the fundus of the subject's eye;
an imaging optical system configured to guide to the imaging unit the emitted infrared light guided to the fundus by the illumination optical system and reflected by the fundus, and the emitted visible light; and
a storage unit configured to store information about an association between the pixel value of the optic papilla in the infrared fundus image to which the infrared light is radiated and the light amount of visible light emitted by the visible light source with which the fundus of the subject's eye is subjected to a predetermined exposure level,
wherein the control unit controls the light amount of visible light emitted by the visible light source based on an electrical signal output by the imaging unit upon reception of the emitted infrared light and the stored information about the association.

17. An ophthalmologic imaging apparatus comprising:
a control unit configured to control, based on a light amount of reflected light from an optic papilla out of light having a first bandwidth band radiated onto a subject's eye, a light amount of light having a second wavelength band different from the first wavelength band to be radiated onto the subject's eye; and
an imaging unit configured to capture an image of the fundus of the subject's eye to which the light having the controlled light amount and the second wavelength band is radiated.

18. A method for controlling an ophthalmologic imaging apparatus, the method comprising:
controlling, based on the light amount of reflected infrared light from an optic papilla out of infrared light radiated onto a subject's eye, the light amount of visible light to be radiated onto the subject's eye; and
capturing an image of the fundus of the subject's eye to which visible light having the controlled light amount is radiated.

* * * * *